United States Patent [19]

Timmerman et al.

[11] Patent Number: 4,694,000
[45] Date of Patent: Sep. 15, 1987

[54] QUINAZOLINE AND ISOQUINOLINE DERIVATIVES

[75] Inventors: Hendrik Timmerman, Voorschoten; Henderikus Van der Goot, Goofddorp, both of Netherlands

[73] Assignee: Akzo N.V., Arnhem, Netherlands

[21] Appl. No.: 679,000

[22] PCT Filed: Sep. 28, 1984

[86] PCT No.: PCT/EP84/00312
§ 371 Date: Dec. 6, 1984
§ 102(e) Date: Dec. 6, 1984

[87] PCT Pub. No.: WO 85/01501
PCT Pub. Date: Apr. 11, 1985

[30] Foreign Application Priority Data

Sep. 29, 1983 [NL] Netherlands ............... 83.03328

[51] Int. Cl.$^4$ ............ A61K 31/47; A61K 31/505; C07D 401/04
[52] U.S. Cl. .................. 514/187; 514/186; 514/253; 514/259; 514/269; 514/274; 514/310; 544/225; 544/284; 544/315; 544/318; 544/319; 544/333; 544/405; 546/2; 546/143
[58] Field of Search .............. 546/143, 2; 544/284, 544/333, 405, 225, 315, 318, 319; 514/253, 259, 269, 310, 186, 187, 274

[56] References Cited

U.S. PATENT DOCUMENTS 3,674,791 7/1972 Mathison ............... 546/143
4,125,724 11/1978 Howell ................ 546/143
4,282,222 8/1981 Bartmann et al. ........ 546/143

OTHER PUBLICATIONS

Eur. J. Med. Chem. –Chim. Ther., 1984–19, No. 5, pp. 389–392, Synthesis and antimycoplasmal activity of 2,2'-bipyridyl analogues, Piet J. Pijper, Henk Van der Goot, Henk Timmerman and Wijbe Th. Nauta.

Linschoten, et al., "Chemical Abstracts.", vol. 101, 1985, Col. 101:110863v (abstract of Eur. J. Med. Chem, vol. 19, No. 2, 1984).

Primary Examiner—Glennon H. Hollrah
Assistant Examiner—James H. Turnipseed
Attorney, Agent, or Firm—Wegner & Bretschneider

[57] ABSTRACT

The invention relates to novel quinazoline and isoquinoline derivatives of the general formula:

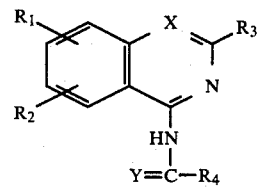

and acid addition salts and copper complexes thereof, wherein
X represents nitrogen or a CH group,
Y represents oxygen or an NH group,
$R_1$ and $R_2$ represent hydrogen, alkyl(1-6 C), alkoxy (1-6 C), halogen or trifluoromethyl,
$R_3$ represents a substituted or unsubstituted 2-pyridyl group and
$R_4$ represents hydrogen, an alkyl(1-6 C) group unsubstituted or substituted by halogen, alkoxy (1-6 C) or phenyl groups, a cyclic alkyl group or a substituted or unsubstituted aromatic group.

33 Claims, No Drawings

QUINAZOLINE AND ISOQUINOLINE DERIVATIVES

The invention relates to novel therapeutically useful quinazoline and isoquinoline derivatives, to processes for the preparation of these derivatives and to pharmaceutical preparations which contain these derivatives as the active constituent.

The quinazoline and isoquinoline derivatives according to the present invention are characterized by the general formula I:

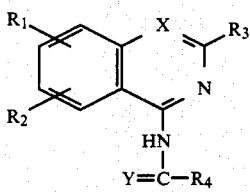

and acid addition salts thereof, wherein
- X represents nitrogen or a CH-group,
- Y represents oxygen or an NH-group,
- $R_1$ and $R_2$ represent hydrogen, alkyl(1–6C), alkoxy(1–6C), halogen or trifluoromethyl,
- $R_3$ represents a substituted or unsubstituted 2-pyridyl group and
- $R_4$ represents hydrogen, an alkyl(1–6C) group which is unsubstituted or substituted by halogen, alkoxy(1–6C) or phenyl groups, a cyclic alkyl group or a substituted or unsubstituted aromatic group.

The compounds according to the general formula I have a biocidal action, in particular against Gram-positive bacteria, protozoa (such as *Trichomonas pulmonalis* and *Trichomonas vaginalis*) and above all pleuropneumonia-type microorganisms, such as mycoplasms, which inter alia can be responsible for the occurrence of pneumonia in cattle and poultry.

The biocidal activity of the compounds in question is moreover further intensified by the addition of copper in the form of a copper compound such as copper sulphate. The addition of an approximately equimolar quantity of copper is preferred, but smaller quantities of copper also already suffice to give a significant intensification of the activity.

The compounds according to formula I can form stabile complexes with copper. These copper complexes form part of the present invention too. These can be formed upon the addition of either $Cu^I$ salts or $Cu^{II}$ salts to the compounds.

The need for novel highly active biocidal compounds is great since in general the microorganisms to be combated, and the mycoplasms in particular, very rapidly develop a certain degree of resistance to the biocidal substances which have already been used for some time in infectious diseases caused by these microorganisms.

The compounds according to the invention can be prepared in the manner customary for such compounds.

The most generally usable method for the preparation of a compound I, wherein Y represents oxygen, consists in the reaction of a 4-amino-quinazoline or 4-amino-isoquinoline derivative of the formula II:

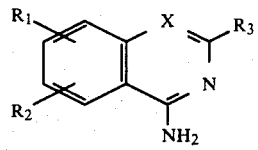

or of a salt thereof, wherein $R_1$, $R_2$, $R_3$ and X have the meaning given above, with a compound of the general formula III:

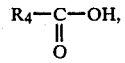

or with an ester, acid halide or acid anhydride derived therefrom, wherein $R_4$ has the meaning given above.

The starting compounds of the general formula II are in the majority of cases known. Where they are not previously known, they can be prepared in the manner known for similar compounds.

The most generally useful method for the preparation of compounds I, wherein Y represents the group NH, consists in the reaction of a 4-halo-quinazoline or isoquinoline compound of the formula IV:

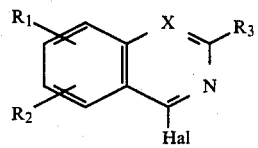

or of a salt thereof, wherein $R_1$, $R_2$, $R_3$ and X have the meaning given above, Hal represents a halogen atom, with an amidine derivative according to the formula V:

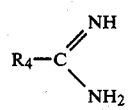

This reaction is preferably carried out under basic reaction conditions.

Another method for the preparation of the compounds I, wherein Y represents an NH group, consists in the reaction of a compound of the general formula VI:

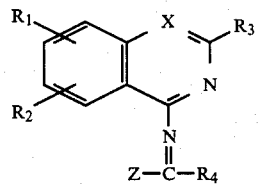

wherein $R_1$, $R_2$, $R_3$ and $R_4$ have the meaning given above and Z represents a halogen, preferably chlorine, or an alkoxy(1–4C) group, with ammonia ($NH_3$).

The last-mentioned method is particularly suitable for the synthesis of compounds I, wherein Y represents an NH group and $R_4$ a substituted or unsubstituted phenyl group or hydrogen.

The starting compound according to the formula VI, wherein Z represents halogen, can inter alia be obtained by halogenating a corresponding compound of the general formula I, wherein Y represents oxygen. The compound VI where $R_4$ is hydrogen and Z is $OC_2H_5$ can be obtained by reacting a compound of the formula II with triethyl orthoformate.

Yet a further method for the preparation of compounds I, wherein Y represents an NH group, consists in the reaction of a compound of the formula II with a nitrile of the formula VII:

$$R_4—C\equiv N \qquad \qquad VII$$

The last-mentioned method is particularly suitable for the preparation of the compounds I, wherein Y is NH and $R_4$ represents a halogen-substituted alkyl group, such as $CF_3$, or a substituted or unsubstituted aromatic group.

Pharmaceutically useful acid addition salts of the compounds I are derived from inorganic acids such as HCl, HBr, sulphuric acid and phosphoric acid, and from organic acids such as acetic acid, oxalic acid, citric acid, maleic acid, fumaric acid and tartaric acid.

By an alkyl group, as referred to in the definitions of $R_1$, $R_2$ and $R_4$, there is meant an alkyl group with 1 to 6 carbon atoms and preferably with 1-4 carbon atoms, such as methyl, ethyl, propyl, isopropyl, butyl, sec.-butyl and tert.-butyl.

The alkyl part of the alkoxy group preferred to in the definitions of $R_1$, $R_2$ and $R_4$ has the same meaning as that described above for the alkyl group.

By a substituted or unsubstituted 2-pyridyl group in the definition of $R_3$ there is meant a 2-pyridyl group which is unsubstituted or can be substituted by alkyl(-1-6C), alkoxy(1-6C) or halogen.

By a cyclic alkyl group (in the definition of $R_4$) there is meant a cycloalkyl or cycloalkyl-alkyl group of 3-8 carbon atoms, such as cyclobutylmethyl, cyclopentyl, cyclohexyl and cyclooctyl.

By an unsubstituted aromatic group (in the definition of $R_4$) there is meant an aromatic hydrocarbon group, such as phenyl or naphthyl, or a hetero-aromatic group, such as pyridyl (2-, 3- or 4-pyridyl), pyrimidinyl, pyrazinyl, furyl, thienyl, oxazolyl and thiazolyl. By a substituted aromatic group there is meant an aromatic group, defined above, which is substituted by alkyl(1-6C), alkoxy(1-6C) or halogen.

For therapeutic purposes the compounds according to the invention can be administered either orally or parenterally, optionally mixed with a customary pharmacologically acceptable carrier.

For veterinary administration, the compounds according to the invention can most simply be administered together with the feed.

The recommended daily dose can, depending on the disease to be combated and on the species of animal, vary from 0.1 to 10 mg per kg of body weight; the preferred dose is between 0.25 and 1 mg per kg body weight per day.

Compounds according to the formula I which are particularly preferred are the compounds wherein, optionally in combination with one another, (a) X represents nitrogen,
(b) Y represents an NH group and
(c) $R_4$ represents a 2-pyridyl group or a $CF_3$ group.

The biocidal activity of compounds according to the invention is, globally, intensified by a factor of 10-1,000 if copper is present, either as a non-toxic quantity of a copper compound or copper salt mixed with the compound according to the invention, or bonded to the latter as a copper-complex.

EXAMPLES

A. Synthesis of some starting compounds

1. 4-Amino-2-(2-pyridyl)-quinazolines 16.6 g of freshly prepared sodium methoxide (0.31 mole) were added to a solution of 36.3 g of 2-amino-benzonitrile (0.31 mole) in 350 ml of anhydrous dioxane, and the mixture was then stirred under a nitrogen atmosphere until all the sodium methoxide had dissolved. Thereafter 32.2 g of 2-pyridinecarbonitrile (0.31 mole) were added dropwise with stirring. The reaction mixture was boiled for 15 hours under a reflux condenser. After the mixture had cooled, 25 ml of water were added, followed by 60 ml of 36-38% strength hydrochloric acid (0.6 mole). The resulting solution was evaporated to dryness and the residue was dissolved in water; after addition of chloroform, the reaction mixture was neutralised. The chloroform layer was separated off and the water layer was washed three times with chloroform. The combined chloroform layers were washed with water, dried and evaporated to dryness. The residue was recrystallised twice from methanol-/ethyl acetate.

41.7 g (61%) of 4-amino-2-(2-pyridyl)-quinazoline were obtained as cream-coloured needles of melting point 173°–174° C.

2. 2-(2-pyridyl)-quinazolin-4(3H)-one 21.1 g (0.09 mole) of the product obtained under 1. were dissolved in 500 ml of 1N hydrochloric acid and the solution was boiled for 65 hours under a nitrogen atmosphere. After it had cooled to room temperature, 300 ml of chloroform were added. The mixture was then neutralised with ammonia. The water layer was extracted twice with chloroform. The combined chloroform layers were washed with water, dried and evaporated to dryness. The residue was recrystallised from ethanol; yield 16.8 g (79%) of white flakes, of melting point 168°–169° C.

3. 4-Chloro-2-(2-pyridyl)-quinazoline 15.0 g (0.067 mole) of the compound obtained under 2., suspended in a mixture of 300 ml of freshly distilled phosphorus oxychloride and 20.4 g of phosphorus pentachloride (0.1 mole), were boiled for four hours under a nitrogen atmosphere and then evaporated to dryness. 1,000 ml of an ice-cold aqueous saturated sodium bicarbonate solution were then added. When the evolution of gas had ceased, the mixture was extracted twice with chloroform and the combined chloroform layers were dried and evaporated. The resulting oil solidified after standing for some time; yield 15.3 g (94%), melting point 120°–122° C.

B. Synthesis of the compounds according to the invention (formula I)

EXAMPLE 1

N-(2-(2-pyridyl)-quinazolin-4-yl)-acetamide 2.22 g (0.01 mole) of the compound obtained under A.1. were dissolved in 50 ml of acetic anhydride and the solution was boiled for two hours. The resulting reaction mixture was evaporated to dryness. NMR-analysis of the mixture after evaporation to dryness indicated that the starting compound had been selectively acetylated at an endocyclic nitrogen atom. Repeated recrystallisation in butanone gave 0.60 g (23%) of the desired amide as white needles of melting point 171°–175° C.

EXAMPLE 2

N-(2-(2-pyridyl)-quinazolin-4-yl)-benzamide 22.2 g (0.1 mole) of the compound obtained under A.1. were suspended in 250 ml of anhydrous THF. 60 ml of a 1.6 molar solution of butyllithium in n-hexane (0.1 mole) were added dropwise to this suspension at 0° C. under a nitrogen atmosphere. 54.2 g (0.39 mole) of benzoyl chloride in 125 ml of THF were then added slowly. When the mixture had come to room temperature, it was boiled for four hours under a reflux condenser. The resulting mixture was evaporated and 250 ml of water were then added. Chloroform was then added and the whole was brought to pH 9. The two-phase system was then stirred for one hour, the chloroform layer separated off and the water layer extracted twice more with chloroform.

The combined chloroform layers were washed with water, dried and evaporated to dryness, and the mixture thus obtained was successively recrystallised from chloroform/ethyl acetate and chloroform/petroleum ether (100–140). This gave 13.0 g (40%) of the desired product as cream-coloured flakes of melting point 203°–204° C.

EXAMPLE 3

N-(2-(2-pyridyl)-quinazolin-4-yl)-trifluoroacetamide

This synthesis was carried out according to Example 1, starting from 4.44 g (0.02 mole) of the product obtained according to A.1. and 15 ml (0.05 mole) of trifluoroacetic anhydride. In this case the reaction mixture was not boiled under reflux but was kept at room temperature. The residue was recrystallised from chloroform. Yield 3.9 g (61%) of the desired product in the form of white needles of melting point 245°–248° C.

EXAMPLE 4

The following were also prepared in a corresponding manner to that described in Example 1:
N-(2-(2-pyridyl)-quinazolin-4-yl)-benzamide
N-(3-(2-pyridyl)-isoquinolin-1-yl)-benzamide
N-(3-(2-pyridyl)-isoquinolin-1-yl)-acetamide.

EXAMPLE 5

N-(2-(2-pyridyl)-quinazolin-4-yl)-formamidine 0.25 ml of sulphuric acid was added to 50 ml of triethylorthoformate and the mixture was stirred for five minutes. 4.44 g (0.02 mole) of the compound obtained under A.1. were than added and the resulting suspension was boiled for three hours under a reflux condenser. After neutralisation of the acid by addition of sodium carbonate, the mixture was concentrated in vacuo and 250 ml of ammonia-containing chloroform were added. The inorganic material was filtered off and anhydrous ammonia was passed through the solution. After about half an hour, a white solid separated out of the solution. The mixture was left overnight, after which the precipitate was filtered off, boiled for some hours in chloroform and filtered off hot. Yield 3.0 g (60%), melting point 187°–188° C.

EXAMPLE 6

N-(2-(2-pyridyl)-quinazolin-4-yl)-acetamidine 0.97 g (0.024 mole) of potassium was added to 200 ml of liquid ammonia, with ferric nitrate as the catalyst. 1.2 g of acetamidine hydrochloride (0.012 mole) were cautiously added to the resulting potassium amide suspension and the reaction mixture was stirred for two hours. 3.0 g (0.012 mole) of the product obtained under A.3., dissolved in the minimum amount of anhydrous dioxane, were then added dropwise. The mixture was boiled for four hours under reflux, with stirring. An excess of ammonium chloride was then added and the ammonia liberated was allowed to evaporate. Thereafter, chloroform and water were added and the pH was brought to 8. The chloroform layer was separated off and the water layer was extracted twice more with chloroform. The combined chloroform layers were washed with water, dried and evaporated. The residue was recrystallised from ethyl acetate/butanone. Yield 0.70 g (21%) of the desired product, as cream-coloured needles; melting point 172°–173° C.

EXAMPLE 7

The following were prepared analogously to Example 6:
N-(2-(2-pyridyl)-quinazolin-4-yl)-benzamidine;
N-(3-(2-pyridyl)-isoquinolin-1-yl)-benzamidine;
N-(3-(2-pyridyl)-isoquinolin-1-yl)-acetamidine;
N-(2-(2-pyridyl)-quinazolin-4-yl)-pyridine-2-carboxamidine.

EXAMPLE 8

N-(2-(2-pyridyl)-quinazolin-4-yl)-trifluoroacetamidine 18.75 ml of a 1.6N solution of butyl-lithium in n-hexane (0.03 mole) were added dropwise at 0° C. to 6.66 g (0.03 mole) of the compound obtained under A.1., suspended in 100 ml of anhydrous THF. 4.0 of trifluoroacetonitrile (0.04 mole) were then passed slowly through the reaction mixture. The reaction mixture was then brought to room temperature and left thereat overnight. Water was then added, the THF was evaporated off, chloroform was added and the pH was brought to 8. The resulting layers were separated and the water layer was extracted twice more with chloroform. The combined chloroform layers were washed with water, dried and evaporated. The residue was recrystallised from ethanol. Yield 3.77 g (40%) of cream-coloured needles, melting point 189° C. (monohydrate).

EXAMPLE 9

The following were prepared in a corresponding manner to that described in Example 8:
N-(2-(2-pyridyl)-quinazolin-4-yl)-pyridine-2-carboxamidine;
N-(3-(2-pyridyl)-isoquinolin-1-yl)-pyridine-2-carboxamidine.

EXAMPLE 10

N-(2-(2-pyridyl)-quinazolin-4-yl)-benzamidine 4.16 g of phosphorous pentachloride were dissolved in 50 ml of chloroform, after which a solution of 3.26 g of N-(2-(2-pyridyl)-quinazolin-4-yl)-benzamide (Example 2) in 20 ml of chloroform was added dropwise. The mixture was then boiled for 5 minutes under reflux.

Thereafter the mixture was cooled to room temperature and ammonia was then passed through it.

After one hour, a cold saturated sodium bicarbonate solution was added slowly, after which the chloroform layer was separated off, washed and evaporated to dryness. The residue obtained was recrystallised from ethyl acetate methanol. Yield 2.9 g (90%); melting point 205°–206° C.

We claim:

1. Compound of the formula:

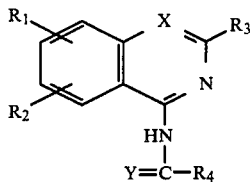

and pharmaceutically acceptable acid addition salts and copper complexes thereof, wherein
X represents nitrogen or a CH group,
Y represents oxygen or an NH group,
$R_1$ and $R_2$ represent hydrogen, alkyl(1–6C), alkoxy(1–6C), halogen or trifluoromethyl,
$R_3$ represents a 2-pyridyl group which is unsubstituted or substituted by alkyl(1–6C), alkoxy(1–6C) or halogen,
$R_4$ represents hydrogen, an alkyl(1–6C) group which is unsubstituted or substituted by halogen, alkoxy(1–6C) or phenyl groups, a cyclic alkyl group (3–8C) or an aromatic group selected from phenyl, naphthyl, pyridyl, pyrimidyl, pyrazinyl, furyl, thienyl, oxazolyl and thiazolyl, which aromatic group is unsubstituted or substituted by alkyl(1–6C), alkoxy(1–6C) or halogen.

2. Compounds according to claim 1, wherein $R_3$ represents an unsubstituted 2-pyridyl group.

3. Compounds according to claim 1, wherein X represents a nitrogen atom, Y represents an NH group and $R_4$ represents a trifluoromethyl or pyridyl group.

4. Compounds according to claim 2, wherein X represents a nitrogen atom, Y represents an NH group and $R_4$ represents a trifluoromethyl or pyridyl group.

5. Compound of claim 1 wherein X is a nitrogen atom.

6. Compound of claim 1 wherein Y is NH.

7. Compound of claim 1 wherein $R_4$ is trifluoromethyl or pyridyl.

8. Compound of the formula:

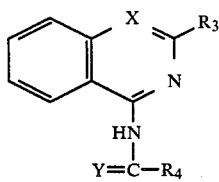

and pharmaceutically acceptable acid addition salts and copper complexes thereof, wherein
X represents nitrogen or a CH group,
Y represents oxygen or an NH group,
$R_3$ represents a 2-pyridyl group,
$R_4$ represents hydrogen, an alkyl(1–6C) group which is unsubstituted or substituted by halogen, alkoxy(1–6C) or phenyl groups, a cyclic alkyl group (3–8C) or an aromatic group selected from phenyl, naphthyl, pyridyl, which aromatic group is unsubstituted or substituted by alkyl(1–6C), alkoxy(1–6C) or halogen.

9. A compound according to claim 8 wherein X represents a nitrogen atom, Y represents an NH group and $R_4$ represents a trifluoromethyl or pyridyl group.

10. Compound of claim 8 wherein X is a nitrogen atom.

11. Compound of claim 8 wherein Y is NH.

12. Compound of claim 8 wherein $R_4$ is trifluoromethyl or pyridyl.

13. Feed mixture, characterised in that it contains a biocidally effective amount of a biocide compound according to claim 1.

14. Feed mixture, characterized in that it contains a biocidally effective amount of a biocide compound of claim 2.

15. Feed mixture, characterized in that it contains a biocidally effective amount of a biocide compound of claim 3.

16. Feed mixture, characterized in that it contains a biocidally effective amount of a biocide compound of claim 9.

17. Feed mixture of claim 13 containing a non-toxic quantity of copper in the form of a copper compound or a copper salt able to form a copper complex with the biocide compound.

18. Feed mixture of claim 14 containing a non-toxic quantity of copper in the form of a copper compound or a copper salt able to form a copper complex with the biocide compound.

19. A feed mixture characterized in that it contains a compound of claim 8.

20. A feed mixture characterized in that it contains a compound of claim 9.

21. Feed mixture of claim 19 containing a non-toxic quantity of copper in the form of a copper compound or a copper salt able to form a copper complex with the biocide compound.

22. Feed mixture of claim 20 containing a non-toxic quantity of copper in the form of a copper compound or a copper salt able to form a copper complex with the biocide compound.

23. Pharmaceutical preparation which contains, as the active constituent, a biocidally effective amount of a compound of claim 1 and a carrier or vehicle.

24. Pharmaceutical preparation which contains, as the active constituent, a biocidally effective amount of a compound of claim 2 and a carrier.

25. Pharmaceutical preparation which contains, as the active constituent, a biocidally effective amount of a compound of claim 3 and a carrier.

26. Pharmaceutical preparation which contains, as the active constituent, a biocidally effective amount of a compound of claim 4 and a carrier.

27. Pharmaceutical preparation which contains, as the active constituent, a biocidally effective amount of a compound of claim 8 and a carrier or vehicle.

28. Biocidal preparation which contains, as the active constituent, a biocidally effective amount of a biocide compound of claim 1 and a non-toxic quantity of copper in the form of a copper compound or a copper salt able to form a copper complex with the biocide compound.

29. Biocidal preparation which contains, as the active constituent, a biocidally effective amount of a biocide compound of claim 2 and a non-toxic quantity of copper in the form of a copper compound or a copper salt able to form a copper complex with the biocide compound.

30. Biocidal preparation which contains, as the active constituent, a biocidally effective amount of a biocide compound of claim 3 and a non-toxic quantity of copper in the form of a copper compound or a copper salt able to form a copper complex with the biocide compound.

31. Biocidal preparation which contains, as the active constituent, a biocidally effective amount of a biocide compound of claim 4 and a non-toxic quantity of copper in the form of a copper compound or a copper salt able to form a copper complex with the biocide compound.

32. Biocidal preparation which contains, as the active constituent, a biocidally effective amount of a biocide compound of claim 8 and a non-toxic quantity of copper in the form of a copper compound or a copper salt able to form a copper complex with the biocide compound.

33. Biocidal preparation which contains, as the active constituent, a biocidally effective amount of a biocide compound of claim 9 and a non-toxic quantity of copper in the form of a copper compound or a copper salt able to form a copper complex with the biocide compound.

* * * * *